United States Patent
Cotting et al.

(10) Patent No.: US 6,262,259 B1
(45) Date of Patent: Jul. 17, 2001

(54) METHOD FOR PREPARING LACTAM

(75) Inventors: Marie-Christine Cotting, Bron; Laurent Gilbert; Nathalie Laurain, both of Lyon; Christophe Nedez, Asnieres-sur-Seine, all of (FR)

(73) Assignee: Rhoneapoulenc Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 08/875,451

(22) PCT Filed: Jan. 22, 1996

(86) PCT No.: PCT/FR96/00102

§ 371 Date: Oct. 28, 1999

§ 102(e) Date: Oct. 28, 1999

(87) PCT Pub. No.: WO96/22974

PCT Pub. Date: Aug. 1, 1996

(30) Foreign Application Priority Data

Jan. 27, 1995 (FR) .................................................. 95 01183

(51) Int. Cl.⁷ ................................................. C07D 201/08
(52) U.S. Cl. .............................................................. 540/539
(58) Field of Search ................................................. 540/539

(56) References Cited

U.S. PATENT DOCUMENTS

| 2,357,484 | 9/1944 | Martin ................................. 260/239 |
| 4,625,023 | 11/1986 | Mares et al. .......................... 540/539 |
| 4,628,085 | 12/1986 | Mares et al. .......................... 540/539 |
| 5,493,021 | * 2/1996 | Barratt et al. ........................ 540/539 |

FOREIGN PATENT DOCUMENTS

| 201578 | 1/1959 | (DE) . |
| 43 19 134 | 12/1994 | (DE) . |
| 43 39 648 | 5/1995 | (DE) . |
| 0015801 | 9/1980 | (EP) . |
| 0 097 539 | 1/1984 | (EP) . |
| 0 150 295 | 8/1985 | (EP) . |
| 0 151 440 | 8/1985 | (EP) . |
| 0 659 741 | 6/1995 | (EP) . |
| 1 166 597 | 11/1958 | (FR) . |
| 2 029 540 | 10/1970 | (FR) . |

OTHER PUBLICATIONS

Ullmann's Encyclopedia of Industrial Chemistry, Fifth, Completely Revised Edition, vol. A1.

* cited by examiner

*Primary Examiner*—Bruck Kifle
(74) *Attorney, Agent, or Firm*—Burns, Doane, Swecker & Mathis, L.L.P.

(57) ABSTRACT

The present invention includes a process for the preparation of a lactam by vapor phase reaction of an aliphatic aminonitrile with water in the presence of a solid catalyst, wherein the catalyst is an alumina having a specific surface, measured by the BET method, greater than or equal to 10 $m^2/g$. The alumina catalyst is further characterized by either: (a) a specific surface less than or equal to 280 $m^2/g$, and a volume of pores with a diameter greater than 500 Å which is greater than or equal to 10 ml/100 g; or (b) a specific surface greater than or equal to 50 $m^2/g$ and less than or equal to 280 $m^2/g$, and a volume of pores with a diameter greater than 70 Å which is greater than or equal to 30 $m^2/g$.

11 Claims, No Drawings

METHOD FOR PREPARING LACTAM

The present invention relates to the preparation of a lactam by cyclizing hydrolysis of the corresponding aminonitriles.

Aliphatic lactams, such as in particular epsilon-caprolactam, are base compounds for the preparation of polyamides (polyamide 6 from caprolactam).

One of the known means for preparing these lactams consists in carrying out a cyclizing hydrolysis of the corresponding aminonitriles, more particularly of unbranched aliphatic aminonitriles, by passing in the vapour phase with water over a solid catalyst.

Thus, U.S. Pat No. 2,357,484 describes a process for vapour phase lactam preparation, which consists in passing a mixture of water and aminonitrile over a dehydration catalyst, such as activated alumina, silica gel or boron phosphate.

U.S. Pat. No. 4,628,085 has provided a process for vapour phase lactam preparation, which consists in bringing an aliphatic or aromatic aminonitrile and water into contact with a silica-based catalyst, in the form of spherical particles having a BET surface greater than 250 m$^2$/g and a mean pore diameter less than 20 nm, and generally in the presence of hydrogen and ammonia.

The catalysts used in the processes of the prior art can make it possible, if appropriate, to, obtain good selectivities towards lactam. On the other hand, their deactivation can also be fast, which constitutes a very great handicap in an industrial implementation of the said processes.

In addition, the process according to U.S. Pat. No. 4,628,085 uses a very complex reaction mixture, requiring, at the end of the reaction, separation and recycling operations which greatly complicate the said process.

The present invention provides new alumina catalysts which, while resulting in good selectivity in the reaction for conversion of aminonitriles to lactams, have a long lifetime and therefore require less frequent regeneration.

More precisely, the invention consists of a process for the preparation-of lactams by vapour phase reaction of an aliphatic aminonitrile of general formula (I):

$$N\equiv C-R-NH_2 \qquad (I)$$

in which R represents an alkylene radical having from 3 to 12 carbon atoms, with water in the presence of a solid catalyst, characterized in that the catalyst is an alumina having a specific surface, measured by the BET method, greater than or equal to 10 m$^2$/g.

The alumina used in the process of the invention preferably has a specific surface equal to or less than 500 m$^2$/g.

The most important among the aminonitriles of formula (I) are those which result in lactams which serve as starting material in the preparation of polyamides 4, 5, 6 and 10, that is to say those in the formula of which the symbol R represents a linear alkylene radical having 3, 4, 5 or 9 carbon atoms.

The preferred compound of formula (I) is 6-aminocapronitrile (or epsilon-aminocapronitrile), which results in caprolactam, the polymerization of which provides polyamide 6.

The aluminas which can be used in the present process are first of all aluminas having a specific surface greater than or equal to 10 m$^2$/g and less than or equal to 280 m$^2$/g, as well as a volume for the pores with a diameter greater than 500 angstroms which is greater than or equal to 10 ml/100 g.

The BET specific surface is a specific surface determined by nitrogen adsorption in accordance with ASTM standard D 3663-78 based on the Brunauer-Emmett-Teller method described in the periodical "The Journal of the American Society", 60, 309 (1938).

The volume for the pores with a diameter greater than 500 Å represents the cumulative volume created by all the pores with a size greater than a diameter of 500 Å. This volume is measured by the mercury penetration technique, in which Kelvin's law is applied.

The aluminas of this first family preferably exhibit a volume for the pores with a diameter greater than 500 Å which is greater than or equal to 20 ml/100 g and more preferentially still greater than or equal to 30 ml/100 g.

The aluminas of this first family also preferably exhibit a specific surface greater than or equal to 50 m$^2$/g.

The aluminas which-can be used in the present process are also aluminas having a specific surface greater than or equal to 50 m$^2$/g and less than or equal to 280 m$^2$/g, as well as a volumne for the pores with a diameter greater than 70 angstroms which is greater than or equal to 30 ml/100 g.

The aluminas of this second family preferably exhibit a volume for the pores with a diameter greater than 70 Å which is greater than or equal to 45 ml/100 g.

The aluminas of this second family also preferably exhibit a specific surface greater than or equal to 80 m$^2$/g.

The aluminas which can be used in the present process are also aluminas having a specific surface greater than or equal to 280 m$^2$/g and a total pore volume greater than or equal to 15 ml/100 g.

The aluminas of this third family preferably exhibit a total pore volume greater than or equal to 22 ml/100 g and more preferentially still greater than or equal to 30 ml/100 g.

The aluminas are also characterized by their acidity.

This acidity can be measured by the test of isomerization of 1-butene to 2-butene.

This test is based on the isomerization reaction of 1-butene to a mixture of cis-2-butene and trans-2-butene at a temperature T (T=400° C. in the present case).

The isomerization reaction is a thermodynamic equilibrium. Two constants may be defined:

the theoretical equilibrium constant Kth(T) determined by the calculation:

$$Kth(T) = \frac{[\text{cis-2-butene}]eq + [\text{trans-2-butene}]eq}{[\text{1-butene}]eq + [\text{cis-2-butene}]eq + [\text{trans-2-butene}]eq}$$

where [butene]eq represents the concentration of each of the isomers in equilibrium at the temperature T;

the true equilibrium constant K(T) determined by the result of the measurements:

$$K(T) = \frac{[\text{cis-2-butene}] + [\text{trans-2-butene}]}{[\text{1-butene}] + [\text{cis-2-butene}] + [\text{trans-2-butene}]}$$

where [butene] represents the concentration of each of the isomers at the outlet of the reactor at the temperature T.

The isomerizing power A of the alumina is defined by the activity with respect to the equilibrium:

$$A(T) = \frac{K(T)}{Kth(T)} \times 100$$

In practice, the test is carried out in a vapour phase reactor, operating in pulsed mode, into which 500 mg of ground alumina (particles of between 400 and 500 µm) are introduced. The alumina is conditioned for 2 hours at 250° C. under a helium stream with a flow rate of 2.5 liters/hour. The alumina is then brought to a temperature of 400° C. and 1 milliliter of 1-butene is injected into the helium flow upstream of the alumina. Analysis of the output gases is carried out by gas phase chromatography and makes it possible to measure the amounts of 1-butene and of cis- and trans-2-butene recovered.

This isomerizing power A is corrected for the isomerizing power obtained under the same conditions with the empty reactor. The corrected isomerizing power $A_c$ represents the acidity of the said aluminas.

When the alkali metal or alkaline-earth metal content present in the alumina is less than 60 mmol per 100 g of alumina, the higher the $A_c$ value, the greater the acidity of the alumina.

Generally, the aluminas are obtained by dehydration of gibbsite, of bayerite, of nordstrandite or of their various mixtures. Reference may be made, for example, to the Kirk-Othmer encyclopedia, volume 2, pages 291–297.

The aluminas used in the present process can be prepared by bringing a hydrated alumina, in finely divided form, into contact with a hot gas stream at a temperature of between 400° C. and 1000° C., then keeping the hydrate and the gases in contact for a period ranging from a fraction of a second up to 10 seconds and finally separating the partially dehydrated alumina and the hot gases. Reference may in particular be made to the process described in U.S. Pat. No. 2,915,365.

It is also possible to carry out the autoclaving of agglomerates of the aluminas obtained above, in aqueous medium, optionally in the presence of acid, at a temperature greater than 100° C. and preferably of between 150° C. and 250° C., for a period preferably of between 1 and 20 hours, then to dry them and to calcine them.

The calcination temperature is adjusted so that specific surfaces and pore volumes situated within the ranges of values indicated above are obtained.

Due to their main manufacturing processes, the aluminas used in the present process most often contain sodium, the content of which is usually expressed as weight of $Na_2O$ with respect to the weight of the alumina.

The catalyst can be used in various forms, such as powder, balls, crushed material, extrudates or pellets, it optionally being possible for the shaping to be carried out using a binder.

It can first of all be alumina balls resulting from an oil-drop shaping (or coagulation as drops). This type of ball can, for example, be prepared by a process according to the teaching of Patents EP-A-0,015,801 or EP-A-0,097,539. Control of the porosity can be carried out, in particular, according to the process described in Patent EP-A-0,097, 539, by coagulation as drops of an aqueous alumina suspension or dispersion or of a solution of a basic aluminium salt which is provided in the form of an emulsion composed of an organic phase, of an aqueous phase and of a surfactant or of an emulsifier. The said organic phase can, in particular, be a hydrocarbon.

It can also be crushed alumina materials. These crushed materials can be the result of the crushing of any type of alumina-based material such as, for example, balls obtained by all types of process (oil-drop, bowl granulator or rotating drum) or extrudates. Control of the porosity of these crushed materials is achieved by the choice of the alumina-based material which is crushed in order to produce them.

It can also be alumina extrudates. The latter can be obtained by kneading and then extruding an alumina-based material, it being possible for the said material to result from the rapid dehydration of hydrargillite or from the precipitation of an alumina gel. Control of the porosity of these extrudates can be achieved by the choice of the alumina used and by the preparation conditions for this alumina or by the kneading conditions for this alumina before extrusion. The alumina can thus be mixed during kneading with pore-forming agents. The extrudates can, by way of example, be prepared by the process described in U.S. Pat. No. 3,856, 708.

It can, in certain cases, be advantageous for at least part of the free volume of the reactor to be occupied by an inert solid, such as for example quartz, in order to promote evaporation and dispersion of the reactants.

The cyclizing hydrolysis reaction requires the presence of water. The molar ratio of water to aminonitrile charged is usually between 0.5 and 50 and preferably between 1 and 20. The upper value of this ratio is not critical for the invention but higher ratios are not really advantageous for economical reasons.

The aminonitrile and the water can be charged in the form of their mixtures in the vapour state or can be introduced separately into the reactor. A pre-evaporation of the reactants can be carried out, which reactants then move into a mixing chamber.

It is possible without disadvantage to use any inert gas as carrier, such as nitrogen, helium or argon.

The temperature at which the process of the invention is implemented must be sufficient for the reactants to be definitely in the vapour state. It is generally between 200° C. and 450° C. and preferably between 250° C. and 400° C.

The contact time between the aminonitrile and the catalyst is not critical. In particular, it can vary according to the equipment used. This contact time is preferably between 0.5 and 200 seconds and more preferentially still between 1 and 100 seconds.

The pressure is not a critical parameter of the process. Thus, it is possible to carry out the process under pressures of $10^{-3}$ bar to 200 bar. The process will preferably be implemented under a pressure of 0.1 to 20 bar.

The use of a solvent which is inert under the reaction conditions, such as for example an alkane, a cycloalkane, an aromatic hydrocarbon or one of the above hydrocarbons in the halogenated form, and thus the presence of a liquid phase in the reaction flow, is not excluded.

The examples which follow illustrate the invention.

EXAMPLES 1 TO 4

10 ml of quartz, 1 ml of the catalyst in the form of a 0.8 to 1.25 micrometre powder (nature of the catalyst shown in Table 1 below) and a further 10 ml of quartz are charged successively to a 20 ml cylindrical reactor made of Pyrex glass which is arranged vertically and which is equipped with heating means, with openings for the input and the output of the gas flows and with a system for injection of the reactants.

The reactor, thus charged, is heated at 400° C. under an air stream (with a flow rate of 1.5 liters/hour) for 2 hours. The reactor is then cooled to 320° C. (chosen reaction temperature) and placed under a nitrogen stream (flow rate of 1 liter/hour).

A mixture of 6-aminocapronitrile (ACN) and of water (ratio by weight 50/50, i.e. a water/ACN molar ratio of 6.2) is then injected, using a pump. The rate of injection of the mixture is 1.2 ml/h.

At the outlet of the reactor, the vapours are condensed in a glass trap at room temperature, over a period of 2 hours.

The final reaction mixture is quantitatively determined by vapour phase chromatography.

The degree of conversion (DC) of the aminocapronitrile, the yield (Y) of caprolactam (CPL) with respect to the converted aminocapronitrile and the activity of the catalyst over 2 hours of reaction, measured as grams of caprolactam formed per milliliter of catalytic bed and per hour, are determined.

The aluminas used as catalysts exhibit the following characteristics:

Alumina 7:
  acidity $A_c$ (400° C.)=62%
  specific surface (SS)=81 $m^2/g$
  0.0714% of $Na_2O$
  volume for the pores with a diameter greater than 500 Å: 27 ml/100 g.

Alumina 6:
  acidity $A_c$ (400° C.)=65%
  SS=244 $m^2/g$
  0.0730% of $Na_2O$
  volume for the pores with a diameter greater than 500 Å: 12 ml/100 g.

Alumina 16:
  acidity $A_c$ (400° C.)=65%
  SS=314 $m^2/g$
  0.3640% of $Na_2O$
  total pore volume: 40 ml/100 g Alumina 10:
  acidity $A_c$ (400° C.)=99%
  SS=217 $m^2/g$
  0.0030% of $Na_2O$
  volume for the pores with a diameter greater than 70 Å: 45 ml/100 g.

The results obtained are collated in Table 1 below.

TABLE 1

| Examples | Catalyst | DC % ACN | Y % CPL | Activity |
| --- | --- | --- | --- | --- |
| Example 1 | alumina 7 | 84.2 | 88.3 | 0.49 |
| Example 2 | alumina 6 | 96.0 | 90.0 | 0.53 |
| Example 3 | alumina 16 | 96.0 | 88.0 | 0.66 |
| Example 4 | alumina 10 | 92.6 | 95.8 | 0.68 |

EXAMPLES 5 TO 7

Examples 1 to 3 are repeated, the change in the activity of the various catalysts being monitored over periods ranging up to 32 hours.

The values of the activity for each catalyst and for increasing reaction periods are collated in Table 2 below.

It may be observed that the aluminas used do not lose their catalytic activity over a period of at least 32 hours.

TABLE 2

| Examples | Alumina Catalyst | Activity of the catalyst for periods of | | | | | | |
| --- | --- | --- | --- | --- | --- | --- | --- | --- |
| | | 4 h | 6 h | 8 h | 10 h | 25 h | 30 h | 32 h |
| Example 5 | Alumina 7 | 0.45 | 0.49 | 0.47 | 0.45 | 0.52 | 0.48 | 0.47 |
| Example 6 | Alumina 6 | 0.47 | 0.54 | 0.58 | 0.59 | 0.73 | 0.73 | 0.72 |
| Example 7 | Alumina 16 | 0.75 | 0.77 | 0.77 | 0.78 | 0.75 | 0.75 | 0.75 |

EXAMPLES 8 TO 21 AND COMPARATIVE TEST 1

2 ml of quartz, 5 ml of the catalyst with a particle size varying from 1 mm to 5 mm and a further 5 ml of quartz are successively charged to a 20 ml cylindrical reactor made of Pyrex glass which is arranged vertically and which is equipped with heating means, with openings for the input and the output of the gas flows and with a system for injection of the reactants.

The reactor, thus charged, is heated at 350° C. under a nitrogen stream (with a flow rate of 5.2 liters/hour) for 2 hours. The reactor is then cooled to 250° C. (chosen reaction temperature) and placed under a nitrogen stream (flow rate of 5.2 liters/hour).

A mixture of 6-aminocapronitrile (ACN) and of water (water/ACN molar ratio of 2.9) is then injected, using a pump. The rate of injection of the liquid mixture is 14 g/h.

At the outlet of the reactor, the vapours are condensed in a glass trap at room temperature over a period of 2 hours.

The final reaction mixture is quantitatively determined by vapour phase chromatography.

The degree of conversion (DC) of the aminocapronitrile, the yield (Y) of caprolactam (CPL) with respect to the converted aminocapronitrile and the activity of the catalyst over 2 hours of reaction, measured as grams of caprolactam formed per gram of catalyst and per hour (activity a) and as grams of caprolactam formed per milliliter of catalytic bed and per hour (activity b), are determined.

The degree of conversion of the ACN varies from 25% to 40% in the various tests and the yield Y of CPL is greater than 90% for Examples 8 to 20 and is 15% for Comparative Test 1.

The characteristics of the aluminas used as catalysts (specific surface=SS, total pore volume=TPV, volume for the pores with a diameter greater than 500 Å=V500 Å, volume for the pores with a diameter greater than 70 Å=V70 Å) and the values of the activities a and b of these various aluminas are shown in Table 3 below.

TABLE 3

| Examples | Alumina | SS $m^2/g$ | TPV ml/100 g | V70 Å ml/100 g | V500 Å ml/100 g | $A_c$ % | Activity a | Activity b |
| --- | --- | --- | --- | --- | --- | --- | --- | --- |
| Example 8 | alumina 1 | 139 | 117 | 116 | 50 | 93 | 2.06 | 0.79 |
| Example 9 | alumina 2 | 192 | 95 | 81 | 52 | 92 | 1.68 | 0.73 |
| Example 10 | alumina 3 | 190 | 72 | 65 | 31 | 92 | 1.32 | 0.66 |
| Example 11 | alumina 4 | 171 | 86 | 80 | 40 | 92 | 1.47 | 0.73 |
| Example 12 | alumina 5 | 333 | 55 | 31 | 20 | 56 | 0.97 | 0.59 |

TABLE 3-continued

| Examples | Alumina | SS m²/g | TPV ml/100 g | V70 Å ml/100 g | V500 Å ml/100 g | $A_c$ % | Activity a | Activity b |
|---|---|---|---|---|---|---|---|---|
| Example 13 | alumina 6 | 244 | 56 | 23 | 12 | 65 | 0.89 | 0.63 |
| Example 14 | alumina 7 | 81 | 68 | 66 | 27 | 62 | 0.86 | 0.44 |
| Example 15 | alumina 8 | 170 | 108 | 105 | 45 | 93 | 1.12 | 0.50 |
| Example 16 | alumina 9 | 115 | 72 | 69 | 29 | 70 | 1.09 | 0.45 |
| Example 17 | alumina 10 | 217 | 55 | 45 | 2 | 99 | 1.10 | 0.65 |
| Example 18 | alumina 11 | 191 | 60 | 58 | 1.5 | 98 | 0.98 | 0.59 |
| Example 19 | alumina 12 | 352 | 43 | 17 | 8 | 84 | 0.91 | 0.59 |
| Example 20 | alumina 13 | 408 | 37 | 14 | 7 | 100 | 0.84 | 0.68 |
| Example 21 | alumina 14 | 350 | 43 | 15 | 6 | 28 | 0.87 | 0.65 |
| Comparative test | alumina 15 | 7.5 | 52 | 52 | 52 | 8 | 0.19 | 0.13 |

EXAMPLES 22 TO 28

3 ml of quartz, 2 ml of the catalyst with a particle size varying from 1 mm to 5 mm and a further 5 ml of quartz are successively charged to the reactor described for the preceding examples.

The reactor, thus charged, is heated at 350° C. under a nitrogen stream (with a flow rate of 5.2 liters/hour) for 2 hours. The reactor is then held at 350° C. (chosen reaction temperature) and placed under a nitrogen stream (flow rate of 5.2 liters/hour).

A mixture of 6-aminocapronitrile (ACN) and of water (water/ACN molar ratio of 1.1) is then injected, using a pump. The rate of injection of the liquid mixture is 11 g/h.

At the outlet of the reactor, the vapours are condensed in a glass trap at room temperature over a period shown in Table 4 below.

The final reaction mixture is quantitatively determined by vapour phase chromatography.

The degree of conversion (DC) of the aminocapronitrile, the yield (Y) of caprolactam (CPL) with respect to the converted aminocapronitrile and the activity of the catalyst over the reaction period, measured as grams of caprolactam formed per gram of catalyst and per hour (activity a) and as grams of caprolactam formed per milliliter of catalytic bed and per hour (activity b), are determined.

The degree of conversion of the ACN is shown in Table 4 and the yield Y of CPL is greater than 90% for Examples 22 to 28.

The values of the activities a and b of these various aluminas are shown in Table 4.

TABLE 4

| Examples | Alumina | Activity a | Activity b | DC % ACN | Period of the test |
|---|---|---|---|---|---|
| Example 22 | Alumina 1 | 8.1 | 3.0 | 66 | 52 h |
| Example 23 | Alumina 2 | 7.0 | 2.9 | 65 | 52 h |
| Example 24 | Alumina 4 | 5.4 | 2.7 | 59 | 49 h |
| Example 25 | Alumina 6 | 4.5 | 2.6 | 56 | 48 h |
| Example 26 | Alumina 7 | 3.3 | 2.0 | 44 | 69 h |
| Example 27 | Alumina 10 | 4.7 | 2.7 | 59 | 48 h |
| Example 28 | Alumina 12 | 3.6 | 2.6 | 54 | 48 h |

What is claimed is:

1. Process for the preparation of a lactam by vapour phase reaction of an aliphatic aminonitrile of general formula (I):

$$N \equiv C - R - NH_2 \qquad (I)$$

in which R represents an alkylene radical having from 3 to 12 carbon atoms, with water in the presence of a solid catalyst, wherein the catalyst is an alumina having a specific surface, measured by the BET method, greater than or equal to 10 m²/g, chosen from:

a) aluminas having a specific surface less than or equal to 280 m²/g, as well as a volume for the pores with a diameter greater than 500 angstroms which is greater than or equal to 10 ml/100 g; and b) aluminas having a specific surface greater than or equal to 50 m²/g and less than or equal to 280 m²/g, as well as a volume for the pores with a diameter greater than 70 angstroms which is greater than or equal to 30 ml/100 g.

2. Process according to claim 1, wherein the alumina used is chosen from aluminas exhibiting a volume for the pores with a diameter greater than 500 Å which is greater than or equal to 20 ml/100 g and more preferentially greater than or equal to 30 ml/100 g.

3. Process according to claim 1, wherein the alumina used is chosen from aluminas exhibiting a specific surface greater than or equal to 50 m² /g.

4. Process according to claim 1, wherein the alumina used is chosen from aluminas exhibiting a volume for the pores with a diameter greater than 70 Å which is greater than or equal to 45 ml/100 g.

5. Process according to claim 1, wherein the alumina used is chosen from aluminas exhibiting a specific surface greater than or equal to 80 m²/g.

6. Process according to claim 1, wherein the aminonitrile of formula (I) is 6-aminocapronitrile.

7. Process according to claim 1, wherein the molar ratio of water to aminonitrile charged is between 0.5 and 50.

8. Process according to claim 1, wherein the temperature at which it is implemented is between 200° C. and 450° C.

9. Process according to claim 2, wherein the alumina used is chosen from aluminas exhibiting a volume for the pores with a diameter greater than 500 Å which is greater than or equal to 30 ml/100g.

10. Process according to claim 7, wherein the molar ratio of water to aminonitrile charged is between 1 and 20.

11. Process according to claim 8, wherein the temperature at which it is implemented is between 250° C. and 400° C.

* * * * *